United States Patent
Bru et al.

(10) Patent No.: US 10,548,834 B2
(45) Date of Patent: Feb. 4, 2020

(54) COMPOSITION INTENDED FOR AN ORAL ADMINISTRATION BASED ON POLYUNSATURATED FATTY ACID AND VITAMIN D FOR IMPROVING HAIR QUALITY

(71) Applicant: NUTRICOS Technologies, Clichy (FR)

(72) Inventors: Carole Bru, Courbevoie (FR); Yann Mahe, Ste Genevieve des Bois (FR); Nathalie Piccardi, Arceau (FR)

(73) Assignee: NUTRICOS TECHNOLOGIES, Clichy (FR)

( * ) Notice: Subject to any disclaimer, the term of this patent is extended or adjusted under 35 U.S.C. 154(b) by 0 days.

(21) Appl. No.: 14/915,362

(22) PCT Filed: Aug. 29, 2014

(86) PCT No.: PCT/EP2014/068450
§ 371 (c)(1),
(2) Date: Feb. 29, 2016

(87) PCT Pub. No.: WO2015/028648
PCT Pub. Date: Mar. 5, 2015

(65) Prior Publication Data
US 2016/0213603 A1    Jul. 28, 2016

(30) Foreign Application Priority Data

Aug. 30, 2013   (FR) ...................... 13 58349

(51) Int. Cl.
| | | |
|---|---|---|
| *A61K 8/92* | (2006.01) | |
| *A61K 8/36* | (2006.01) | |
| *A61Q 5/00* | (2006.01) | |
| *A61K 8/67* | (2006.01) | |
| *A61K 8/27* | (2006.01) | |
| *A61K 8/31* | (2006.01) | |
| *A61K 8/97* | (2017.01) | |
| *A61Q 5/06* | (2006.01) | |
| *A61Q 7/00* | (2006.01) | |

(52) U.S. Cl.
CPC ............... *A61K 8/922* (2013.01); *A61K 8/27* (2013.01); *A61K 8/31* (2013.01); *A61K 8/361* (2013.01); *A61K 8/67* (2013.01); *A61K 8/676* (2013.01); *A61K 8/678* (2013.01); *A61K 8/925* (2013.01); *A61K 8/97* (2013.01); *A61Q 5/00* (2013.01); *A61Q 5/002* (2013.01); *A61Q 5/06* (2013.01); *A61Q 7/00* (2013.01); *A61K 2800/592* (2013.01); *A61K 2800/882* (2013.01); *A61K 2800/92* (2013.01)

(58) Field of Classification Search
CPC ........ A61K 2800/592; A61K 2800/882; A61K 2800/92; A61K 8/27; A61K 8/31; A61K 8/361; A61K 8/67; A61K 8/676; A61K 8/678; A61K 8/922; A61K 8/925; A61K 8/97; A61Q 5/00; A61Q 5/002; A61Q 5/06; A61Q 5/12; A61Q 7/00
See application file for complete search history.

(56) References Cited

U.S. PATENT DOCUMENTS

| | | | |
|---|---|---|---|
| 8,168,611 B1 * | 5/2012 | Perrin ................... | A61K 31/07 514/168 |
| 8,729,033 B2 * | 5/2014 | Giuliani ................ | C07H 17/07 514/27 |
| 2005/0175565 A1 | 8/2005 | Duranton et al. | |
| 2013/0001569 A1 | 1/2013 | Matsumoto et al. | |

FOREIGN PATENT DOCUMENTS

| | | |
|---|---|---|
| EP | 1 932 509 A1 | 6/2008 |
| FR | 1601008 A | 8/1970 |
| WO | WO2009/115769 | * 9/2009 |

OTHER PUBLICATIONS

Life Pharmacy: "Nutra-Life Omega 3 Fish Oil 1500mg Plus Vitamin D 180s", (Feb. 8, 2013).
Swanson Health Products: "Omega Swirl Fish Oil with Vitamin D Mango Peach", (Nov. 30, 2012).
Demchenko et al., "Validated HPTLC Method for Quantification of Vitamin $D_3$ in Fish Oil", Journal of Planar Chromatography, 24 (2011) 6, 487-490.
Skin, Hair & Nails Supplement, GNPD; MINTEL, XP002699673, [Nov. 1, 2008].
Database GNPD [Online], MINTEL; Nov. 2008 (Nov. 2008), "Dietary Supplement with DHA Omega-3", Database accession No. 999084.
Database GNPD [Online], MINTEL; Sep. 2012 (Sep. 2012), "Eye Plus Supplement Eye Sight+Protection", Database accession No. 1864261.
Database GNPD [Online], MINTEL; Jul. 2010 (Jul. 2010), "Hair-Active Capsules", Database accession No. 1357230.
Database GNPD [Online], MINTEL; Jul. 2012 (Jul. 2012), Pure Cod Liver Oil, Database accession No. 1837427.

\* cited by examiner

*Primary Examiner* — Snigdha Maewall
(74) *Attorney, Agent, or Firm* — Polsinelli PC

(57) ABSTRACT

The object of the present invention is the cosmetic use via an oral route of a combination of actives comprising at least one polyunsaturated fatty acid and vitamin D, for improving the hair quality. This combination of actives may further comprise, as an additional active, vitamin E, vitamin C, a carotenoid, zinc gluconate or combinations thereof. The combination of actives is preferably applied in a cosmetic composition intended for oral administration, such as a food supplement.

9 Claims, No Drawings

COMPOSITION INTENDED FOR AN ORAL ADMINISTRATION BASED ON POLYUNSATURATED FATTY ACID AND VITAMIN D FOR IMPROVING HAIR QUALITY

CROSS REFERENCE TO RELATED APPLICATIONS

This application is a National Phase filing under 35 U.S.C. § 371 of PCT/ep2014/068450 filed on Aug. 29, 2014; and this application claims priority to Application No. 1358349 filed in France on Aug. 30, 2013 under 35 U.S.C. § 119. The entire contents of each application are hereby incorporated by reference.

FIELD OF THE INVENTION

The invention relates to the cosmetic use via an oral route of a combination of actives based on polyunsaturated fatty acid and vitamin D for improving hair quality.

STATE OF THE ART

Hair are produced in hair follicles formed with epithelial sheaths of epidermal origin and of a hair bulb containing bulbar keratinocytes in a permanent state of division during the growth phases of the hair. The hair mainly consists of 85-90% of proteins.

Having healthy and strong hair throughout life is sought by most women and men.

For this purpose, there exist many formulations of shampoos, hair conditioners, masks, oils for hair, etc., which directly act on the hair or the scalp. Food supplements ingested orally are also used for the care of hair, for example in order to reduce hair loss or to promote their growth.

The food supplements available on the market are in majority based on vitamin B and sometimes contain vitamin A, vitamin E or vitamin C. In addition to these vitamins, food supplements generally contain sulfur-containing amino acids and/or zinc.

Vitamins B5 and B8 are for example used for preventing hair loss, vitamins B2 and B6 for preventing and treating dandruff and vitamin B3 for stimulating microcirculation. Moreover, sulfur-containing amino acids, such as methionine and cysteine, are used for promoting hair growth.

Finally, zinc is generally used for promoting hair growth. Zinc is indeed necessary for the synthesis of keratin. Its utility was also demonstrated in the prevention of hyperseborrhea and alopecia.

However, consumers are always searching for actives or combinations of efficient actives for improving the quality of their hair and this concerns both women and men of any age.

SUMMARY OF THE INVENTION

The present invention is based on the fact that the inventors have shown that administration via an oral route of vitamin D and of at least one polyunsaturated fatty acid, in particular from fish oil and/or blackcurrant pip oil, gives the possibility of improving the quality of the hair.

Thus, surprisingly, the inventors have shown that cosmetic compositions intended to be administered orally which are not based on vitamin B, but on vitamin D, are useful for improving the quality of the hair.

The inventors have notably applied at least one cosmetic composition which may appear as soft capsules which comprises a combination of actives comprising polyunsaturated fatty acids present as fish oil and blackcurrant pip oil and vitamin D as vitamin D3 and advantageously, vitamin E, vitamin C, a carotenoid, preferably present as a tomato extract, and zinc gluconate.

The administration of the composition above, notably in an amount of two capsules per day, allows improvement in the quality of the hair.

The object of the invention is thus the cosmetic use, via an oral route, of a combination of actives comprising at least one polyunsaturated fatty acid and at least vitamin D, for improving the quality of hair, in particular of men and women.

The object of the invention is particularly the cosmetic use above, wherein the combination of actives is applied within a cosmetic composition suitable for oral administration.

The object of the invention is also a cosmetic composition intended for oral administration comprising:
(i) at least one polyunsaturated fatty acid in a content comprised between 1% and 80% by weight, based on the total weight of the cosmetic composition,
(ii) vitamin D in a content comprised between 0.00001% and 0.15% by weight, based on the total weight of the composition,
(iii) optionally zinc, preferably as zinc gluconate, in a content comprised between 0.001% and 30% by weight, based on the total weight of the composition,
(iv) optionally vitamin E in a content comprised between 0.001% and 10% by weight, based on the total weight of the composition,
(v) optionally vitamin C in a content comprised between 0.001% and 30% by weight, based on the total weight of the composition, and
(vi) optionally a carotenoid in a content comprised between 0.01% and 6% by weight, based on the total weight of the composition.

The object of the present invention is also a cosmetic kit or combination product for simultaneous, separate or spread out in time use, comprising a first cosmetic composition comprising a portion of the compounds forming the combination of actives as defined above and a second cosmetic composition comprising at least the other portion of the compounds forming said combination of actives.

The present invention also relates to a cosmetic method for improving the quality of hair, comprising administration via an oral route to an individual of a combination of actives as defined above, of a cosmetic composition intended for oral administration as defined above, or of a cosmetic kit or combination product as defined above.

DETAILED DESCRIPTION

The main object of the invention is therefore the cosmetic use via an oral route of a combination of actives comprising vitamin D and at least one polyunsaturated fatty acid, in particular from fish oil and/or blackcurrant pip oil, for improving the quality of hair, in particular in men of more than 30 years of age or in women.

Preferably according to the invention, the cosmetic use via an oral route of a combination of actives comprising vitamin D and at least one polyunsaturated fatty acid, in particular from fish oil and/or blackcurrant pip oil, is characterized in that improvement in the quality of the hair comprises the improvement in the gloss of the hair and/or the improvement in the hair styling capability of the hair and/or the reduction in hair loss and/or the improvement in growth of the capillary fiber, in particular thick capillary fibers, and/or the improvement in the volume of the hair and/or the improvement in the quality of the capillary fiber.

By «improving the gloss of the hair», is meant to refer according to the present invention to the fact of promoting less wear and/or improving repair of the scales of the cuticle, in order to homogenize the surface of the hair and to promote reflection of light. Preferentially and according to the invention, the different parameters as defined hereinbefore relative to the improvement in the gloss of the hair may be evaluated by means of a multiple choice questionnaire filled by men and/or women within the scope of an observational study which may be conducted by dermatologists. An effect will be considered as significant from the moment that at least 50% of the men and/or of the women will have perceived a positive effect. The gloss of the hair may also be measured by means a chromameter and is defined by the parameter L* in the CIE Lab system. The CIE Lab system (more specifically L*a*b*) is a model for representing colors developed in 1976 by the International Illumination Commission (CIE).

By «improving the hair styling capability of the hair», is meant to refer according to the invention to hair which is easier to comb and/or to brush, for example by reinforcing, by tightening or smoothing the scales of the hair. Indeed, disconnected or damaged scales hook up with scales of neighboring hair causing entanglement of the hair which then promotes the occurrence of nodes making styling more difficult. By «improving the hair styling capability of the hair», is also meant better holding of the hairstyle after putting on curlers, brushing, coloration, discoloration, hair straightening or curling.

By «ageing of the hair» is meant to refer according to the invention to a change in the aspect of the fiber, for example fine, dull, loose (i.e. limp), hair lacking luster and easily breaking upon combing, hair which tends to fall, which is renewed more slowly, for which the collagen network which supports them is altered by significant release of collagenase and disorganization of its network, the dermal and epithelial portions of which stiffen by the presence of many glycation products (Monnier V M, 1983), for which the sebum synthesis is reduced causing dryness of the scalp and accordingly increasing the dull aspect and lack of luster of the hair, the epidermis and the dermis of the scalp thereof are also subject to disorganization of the collagen network, a significant occurrence of glycation products which stiffen the dermis around the hair follicle causing negative effects for the resident follicles, like gradual miniaturization of the bulbs, and an unfavorable environment for the implantation of new hairs.

By «ageing of the hair» is also meant a reduction in capillary density, as well as in the diameter of the hairs expressed by a reduction of the coverage of the scalp.

The present invention also aims at the cosmetic use via an oral route of a combination of actives comprising at least one polyunsaturated fatty acid and vitamin D in order to combat ageing of the hair and of the perifollicular tissue in contact, in particular in men of more than 30 years of age or in women.

By «preventing loss» or «reducing hair loss», is meant according to the invention a decrease in the percentage of hairs in a telogenous phase and/or a decrease in the percentage of hairs in a loss phase.

A decrease in the percentage of hair in a telogenous phase may be measured with Trichoscan® based on the fact that hair in the telogenous phase no longer grows, unlike hair in an anagenous phase. A reduction of 5% of the number of hairs in the telogenous phase may be considered as significant.

A decrease in the percentage of hair in the loss phase may be measured by means of the trichogram or of the Trichoscan®, or by collecting hair during a hair styling or after the shower based on the fact that the hair in the loss phase are the visible reflection of the hairs engaged previously in the growth stopping phase, i.e. in the telogenous phase, and representing the loss as actually perceived by an individual affected by abnormally high loss of hair. A 5% decrease in the number of hairs in the loss phase may be considered as significant.

By «improvement in the growth of capillary fibers», is meant to refer according to the invention to the increase in the growth of hair. Preferentially and according to the invention, the improvement in the growth of capillary fibers may be evaluated by means of a multiple choice questionnaire filled in by men and/or women, within the scope of an observational study which may be conducted by dermatologists. An effect will be considered as significant from the moment when at least 50% of the men and/or women will have perceived a positive effect. The growth of capillary fibers may also be measured after coloration or discoloration of a strand. The measurement of the distance between the root and the limit of the coloration or discoloration gives the possibility of evaluating the growth of capillary fibers.

By «improvement in the growth of thick capillary fibers», is meant to refer according to the invention to the increase in the growth of hair with a diameter of more than 40 µm. The diameter of the hair may advantageously be measured by means of the automated equivalent Trichoscan® of the trichogram wherein the human eye has been replaced by an image analysis software (Gasmueller, 2009). A 5% increase in the number of hairs with a diameter of more than 40 µm may be considered as significant.

Still preferably, the improvement in the volume of the hair comprises the increase in the diameter of the capillary fiber, and/or the increase in the density, and/or the limitation of the refinement of the capillary fiber.

By «increase in the diameter of the capillary fiber», is meant to refer according to the invention to an increase in the number of hairs having a diameter of more than 40 µm. A 5% increase in the number of hairs with a diameter of more than 40 µm may be considered as significant.

By «increase in the density», is meant according to the invention a larger number of hairs per $cm^2$. The density of the hair is also measurable with the Trichoscan®. With this apparatus, a density of less than 250 hairs per $cm^2$ is considered as low density. A 5% increase in the density may be considered as clinically significant and visible.

By «refinement of the hairs», is meant to refer according to the invention to a reduction in the diameter of the hairs to below 40 µm. The diameter of the hairs may advantageously be measured by means of the automated equivalent Trichoscan® of the trichogram wherein the human eye has been replaced with an image analysis software (Gasmueller, 2009). Moreover, below 40 µm the hairs are visible to the naked eye with difficulty. The refinement of the hairs may therefore be perceived. A 5% reduction in the number of hairs having a diameter below 40 µm may be considered as significant.

By «improving the volume of the hair», is notably meant to refer according to the invention to an increase in the diameter of the hairs associated with a decrease in the heterogeneity of the diameter of the hairs, and to an increase in the density.

The heterogeneity of the diameter of the hairs may be measured by means of a binocular magnifying glass, for example by sorting a strand of 50 to 100 cut (or else removed) hairs by classifying them, for example in four categories (very fine, fine, thick and very thick), and by calculating the percentage of hairs in each category. The heterogeneity of the diameter of the hairs is then evaluated by comparing the time-dependent change in these percentages overtime.

Also preferably, the improvement in the quality of the capillary fiber comprises the tensile strength of the hairs, and/or the prevention and/or the combat against limp and/or fragile and/or dull and/or forked and/or embrittled and/or sensitized and/or dry hairs, and/or improvement in the gentleness and strength of the capillary fibers.

By «preventing and/or combating limp and/or fragile and/or dull and/or forked and/or embrittled and/or sensitized and/or dry hairs», is meant to refer according to the invention to an overall improvement in the structure of the hair shaft and notably of the cuticle, the outmost layer of the hair. The quality of the cuticle may be evaluated, for example by means of a microscope, by noting the presence of narrowed or disconnected scales, of either intact scales or not and/or of broken scales, or even missing scales. A 5% decrease in the number of disconnected, broken or missing scales may be considered as significant.

By «improving the gentleness», is meant to refer according to the invention to an improvement in the condition of the scales of the cuticle and more particularly of their cohesion. Disconnected, broken or missing scales make the hairs rough to the touch. The improvement in gentleness may be evaluated, for example by means of a microscope, by noting the presence of disconnected, broken or missing scales. A 5% decrease in the number of disconnected, broken or missing scales may be considered as significant.

By «improving the tensile strength of the hairs» and «improving the strength of capillary fibers», is meant to refer according to the invention to the solidity of the hairs which may be measured by the tensile test. This measurement for determining mechanical tensile properties of the hair may be conducted by means of a commercial tool, the MTT600 (mini Tensile Tester) from Dia Stron (http://www.diastron.com/). A 5% increase in the force required for breaking the hair is considered as significant.

The different parameters as defined above may be evaluated by means of a multiple choice questionnaire filled in by men and/or women within the scope of an observational study which may be conducted at dermatologists. An effect will be considered as significant from the moment when at least 50% of the men and/or women will have perceived a positive effect.

Men of more than 30 years of age and women are particularly concerned by the uses according to the invention.

By «men», is meant in the sense of the present invention the human male population.

Polyunsaturated Fatty Acids

By «polyunsaturated fatty acid» is meant in the sense of the present invention, a fatty acid comprising at least two double bonds. These are more particularly long chain fatty acids, i.e. having at least 14 carbon atoms.

Polyunsaturated fatty acids may be in acid form, as triglycerides or as methyl or ethyl esters.

Polyunsaturated fatty acids notably comprise ω-3 fatty acids, ω-6 fatty acids and ω-9 fatty acids, characterized by the position of the unsaturation the closest to the terminal methyl group, and mixtures thereof.

Subsequently, the terms of «ω» and «omega» are equally used.

Polyunsaturated fatty acids including from 18 to 22 carbon atoms, more preferentially ω-3, ω-6 and ω-9 fatty acids are most particularly suitable for the invention. From among the polyunsaturated fatty acids of the ω-6 series, mention may in particular be made of linoleic acid with 18 carbon atoms and two unsaturations or LA (18:2, ω-6), γ-linolenic acid with 18 carbon atoms and three unsaturations or GLA (18:3, ω-6), di-homogammalinolenic acid with 20 carbon atoms and 3 unsaturations (20:3, ω-6), arachidonic acid, 5,8,11,14-eicosatetraenoic acid (20:4, ω-6) and docosatetraenoic acid (22:4, ω-6).

The polyunsaturated fatty acids of the ω-3 series may notably be selected from α-linolenic acid or ALA (18:3, ω-3), stearidonic acid or SDA (18:4, ω-3), 5,8,11,14,17-eicosapentaenoic acid or EPA (20:5, ω-3), 4,7,10,13,16,19-docosahexaenoic acid or DHA (22:6, ω-3), docosapentanoic acid or DPA (22,5, ω-3) and n-butyl-5,11,14-eicosatrienonic acid.

The polyunsaturated fatty acids of the ω-9 series may notably be selected from among oleic acid (18:1, ω-9) and erucic acid (22:1, ω-9).

α-linolenic acid, linoleic acid, γ-linolenic acid, stearidonic acid, eicosapentaenoic acid, docosahexaenoic acid, oleic acid, an extract comprising them or their combinations are most particularly suitable for the invention.

According to an alternative of the invention, the relevant polyunsaturated fatty acid(s) is(are) used in an isolated form, i.e. after extraction from its(their) origin sources.

The total content of polyunsaturated fatty acid(s) in a composition according to the invention may vary from 1% to 80% by weight, preferably from 5% to 70% by weight, more preferentially from 10% to 60% by weight, still more preferentially from 20% to 50% by weight based on the total weight of the composition.

For example, a composition according to the invention may comprise a total content of polyunsaturated fatty acid(s) comprised between 35% and 45% by weight.

A composition according to the invention, as developed hereafter, may comprise the polyunsaturated fatty acid(s) in an adjusted concentration so that the polyunsaturated fatty acid(s) is(are) administered at a content ranging from 100 mg/day to 1,500 mg/day, preferably from 200 mg/day to 700 mg/day, more preferentially from 350 mg/day to 550 mg/day.

For example, a composition according to the invention may comprise the polyunsaturated fatty acid(s) in an adjusted concentration so that the polyunsaturated fatty acid(s) is(are) administered at a content ranging from 400 mg/day to 500 mg/day.

The source of polyunsaturated fatty acid may be selected from vegetable oils, such as for example evening primrose oil, borage oil, blackcurrant pip oil, echium oil, hemp oil, an extract from the microalga *Schizochytrium* sp. or combinations thereof. The vegetable source of polyunsaturated fatty acid is preferably blackcurrant pip oil.

The source of polyunsaturated fatty acid may also be selected from fish oils.

Vegetable oils of walnuts, hazelnuts, almonds (*Juglans regia*), coriander and soja (*Glycina max*), rapeseed (*Brassica naptus*), chia, flax and fish oils, for example are rich in polyunsaturated fatty acids of the ω-3 series.

The polyunsaturated ω-3 fatty acids may also be found in zooplankton, crustaceans/shellfish and fish. Fish oils are the main industrial source of EPA and DHA. Microalgae biomasses may also be a raw material for extracting ω-3 polyunsaturated fatty acids.

Thus, a polyunsaturated fatty acid may be applied in a combination of actives according to the invention in the form of at least one oil selected from among evening primrose oil, borage oil, blackcurrant pip oil, walnut oil, soja oil, fish oil, sunflower oil, wheat germ oil, hemp oil, fenugreek oil, echium oil, argan oil, rice bran oil, sesame oil, almond oil, hazelnut oil, chia seed oil, flax oil, olive oil, avocado oil, safflower oil, cameline oil, Sacha Inchi oil, passion fruit oil, raspberry pip oil, cranberry seed oil, bilberry seed oil, *Rubus Chamaemorus* Linne seed oil, sea buckthorn oil, cumin oil, kiwi pip oil, coriander oil, microalgae extract oil, zooplankton extract oil, crustacean and/or shellfish extract oil, or combinations thereof.

Microalgae extract oil is for example a *Schizochytrium* sp. extract oil.

Preferably, this is a blackcurrant pip oil and/or a fish oil, more preferentially a blackcurrant pip oil and a fish oil.

A composition according to the invention, as developed hereafter, may comprise an oil and/or an extract and/or a biomass in a content comprised between 20% and 99% by weight, preferably between 30% and 95% by weight, more preferentially between 50% and 90%, still more preferentially between 60% and 85% based on the total weight of the composition.

For example, a composition according to the invention may comprise an oil and/or an extract and/or a biomass in a content comprised between 80% and 85% by weight based on the total weight of the composition.

A composition according to the invention, as developed hereafter, may comprise an oil and/or an extract and/or a biomass in an adjusted concentration so that said oil and/or extract and/or biomass is administered at a content ranging from 100 mg/day to 5,000 mg/day, preferably from 150 mg/day to 3,000 mg/day, more preferentially from 200 mg/day to 1,000 mg/day.

For example, a composition according to the invention may comprise an oil and/or an extract and/or a biomass in an adjusted concentration so that said oil and/or extract and/or biomass is administered at a content ranging from 200 mg/day to 500 mg/day.

Thus, according to a preferred embodiment, a combination of actives according to the invention comprises at least one oil selected from blackcurrant pip oil and/or fish oil.

According to a further preferred embodiment, a combination of actives according to the invention comprises black currant pip oil and fish oil, preferably in a content comprised between 80% and 85% by weight, for example for administration at a content ranging from 200 mg/day to 500 mg/day.

Vitamin D

Vitamin D is preferably selected from vitamin D3 (also called cholecalciferol), vitamin D2 (ergocalciferol) and mixtures thereof. The vitamin D used in the combination of actives according to the invention is preferably vitamin D3.

A composition according to the invention, as developed hereafter, may comprise vitamin D in a content comprised between 0.00001% and 0.15% by weight, preferably between 0.00005% and 0.10% by weight, and more preferentially between 0.0001% and 0.10% by weight, still more preferentially between 0.0001% and 0.05% by weight based on the total weight of the composition.

For example, a composition according to the invention may comprise vitamin D in a content comprised between 0.0004% and 0.0009% by weight based on the total weight of the composition.

A composition according to the invention, as developed hereafter, may comprise vitamin D in an adjusted concentration so that it is administered at a content ranging from 0.0001 mg/day to 0.05 mg/day, preferably from 0.0005 mg/day to 0.01 mg/day, more preferentially from 0.001 mg/day to 0.005 mg/day For example, a composition according to the invention may comprise vitamin D in an adjusted concentration so that it is administered at a content ranging from 0.002 mg/day to 0.006 mg/day.

Additional Actives

A combination of actives according to the invention may also comprise one or several other additional cosmetic actives.

Advantageously, such an additional cosmetic active may be intended for reinforcing the desired cosmetic effect as described earlier.

Of course, one skilled in the art will ensure selection of the additional actives as well as their amount in such a way that the advantageous properties of the composition according to the invention are not, or substantially not altered by the contemplated addition.

As an additional active which may be used, mention may be made of:
- vitamins other than vitamin D, such as vitamin A, at least one vitamin from the group B, for example vitamin B1 (also called thiamine), vitamin B2 (also called riboflavin), vitamin B3 (also called niacin or vitamin PP), vitamin B5, vitamin B6, vitamin B8, vitamin B9 and vitamin B12, vitamin C, vitamin E,
- antioxidants, such as curcuminoids; carotenoids, notably selected from β-carotene, astaxanthin, zeaxanthin, lutein or compounds containing them such as goji berries; polyphenol compounds, flavonoids like catechins; proanthocyanidins, anthocyanins, OPCS (procyanidolic oligomers); ubiquinones; coffee extracts containing polyphenols and/or diterpenes; chicory extracts; ginkgo biloba extracts; grape extracts rich in proanthocyanidins; pepper extracts; soybean extracts; cocoa; pomegranate; Emblica; CoenzymeQ10; selenium,
- minerals, such as zinc, calcium, magnesium, copper, iron, iodine, manganese, selenium, chromium(III),
- sugars,
- amino acids, notably sulfur-containing amino acids, such as glutathione precursors, selenium amino acids, citrullin,
- phytosterols,
- resveratrol,
- hesperidin, neohesperidin,
- orthosilicic acid, monomethylsilanetriol, and
- mixtures thereof.

In a particularly advantageous embodiment of the invention, the combination of actives comprises, as an additional active, at least one compound selected from a vitamin other than vitamin D, preferably vitamin C or vitamin E, a carotenoid or zinc.

The combination of actives according to the invention may for example comprise as an additional active, at least two compounds, preferably at least three compounds, selected from a vitamin other than vitamin D, preferably vitamin C or vitamin E, a carotenoid or zinc.

In another particular advantageous embodiment of the invention, the combination of actives comprises, as an additional active, at least one compound selected from vitamin C, vitamin E, a carotenoid or zinc.

The combination of actives may for example comprise, as an additional active, at least two compounds or at least three compounds selected from among vitamin C, vitamin E, a carotenoid or zinc, or else these four compounds.

Preferably, the combination of actives according to the invention does not comprise any vitamin B, and/or does not comprise any sulfur-containing amino acid or more generally does not comprise any amino acids.

In an advantageous embodiment, the combination of actives according to the invention does not comprise any minerals other than zinc.

In another advantageous embodiment, the combination of actives according to the invention does not comprise any antioxidants other than carotenoids and/or vitamins, or else does not comprise any antioxidants other than lycopene, vitamin C and vitamin E.

The expression «the combination of actives does not comprise the element X» means here that said combination does not comprise said element X other than the one optionally brought by the compounds comprising the actives of the combination, such as a vegetable oil, a fish oil and/or a tomato extract.

Vitamin C and E

According to further another of its aspects, the present invention relates to a combination of actives comprising at least one polyunsaturated fatty acid, vitamin D and at least one other vitamin selected from vitamin C and vitamin E.

Vitamin E is preferably in the form of tocopherol acetate.

According to further another of its aspects, the present invention relates to a combination of actives comprising at least one fish oil comprising at least one polyunsaturated fatty acid, vitamin D and vitamin C. Preferably, a combination of actives according to the invention comprises at least one fish oil comprising at least one polyunsaturated fatty acid, vitamin D, vitamin C, and also vitamin E.

According to further another of its aspects, the present invention relates to a combination of actives comprising at least one blackcurrant pip oil comprising at least one polyunsaturated fatty acid, vitamin D and vitamin C. Preferably, a combination of actives according to the invention comprises at least one blackcurrant pip oil comprising at least one polyunsaturated fatty acid, vitamin D, vitamin C, and also vitamin E.

According to further another of its aspects, the present invention relates to a combination of actives comprising at least one black currant pip oil and a fish oil, vitamin D and vitamin C. Preferably, a combination of actives according to the invention comprises at least one blackcurrant pip oil and a fish oil, vitamin D, vitamin C, and also vitamin E.

A composition according to the invention, as developed hereafter, may comprise vitamin C in a content comprised between 0.001% and 30% by weight, preferably between 0.01% and 25% by weight, and more preferentially between 0.1% and 20% by weight, still more preferentially between 1% and 15% by weight based on the total weight of the composition.

For example, a composition according to the invention may comprise vitamin C in a content comprised between 2% and 3% by weight based on the total weight of the composition.

A composition according to the invention, as developed hereafter, may comprise vitamin C in an adjusted concentration so that it is administered at a content ranging from 5 mg/day to 100 mg/day, preferably from 10 mg/day to 90 mg/day, more preferentially from 20 mg/day to 80 mg/day.

For example, a composition according to the invention may comprise vitamin C in an adjusted concentration so that it is administered at a content ranging from 25 mg/day to 30 mg/day.

A composition according to the invention, as developed hereafter, may comprise vitamin E in a content comprised between 0.001% and 10% by weight, preferably between 0.01% and 10% by weight, and more preferentially between 0.1% and 5% by weight, still more preferentially between 0.2% and 2% by weight based on the total weight of the composition.

For example, a composition according to the invention may comprise vitamin E in a content comprised between 0.4% and 0.5% by weight based on the total weight of the composition.

A composition according to the invention, as developed hereafter, may comprise vitamin E in an adjusted concentration so that it is administered at a content ranging from 0.1 mg/day to 20 mg/day, preferably from 1 mg/day to 15 mg/day, more preferentially from 2 mg/day to 12 mg/day.

For example, a composition according to the invention may comprise vitamin E in an adjusted concentration so that it is administered at a content ranging from 4 mg/day to 6 mg/day.

Carotenoid

A preferred combination of actives according to the invention comprises at least one carotenoid.

By «carotenoid», within the scope of the present invention is meant both a carotenoid with provitamin A activity, and a carotenoid without any provitamin A activity.

Of course according to the invention, the carotenoid may be a mixture of carotenoids with provitamin A activity and of carotenoids without any provitamin A activity. This mixture may be in any proportion.

According to the invention, the carotenoid with a provitamin A activity may be a mixture of carotenoids with provitamin A activity. This mixture may be in any proportion. From among carotenoids with a provitamin A activity, mention may be made as an example of β-carotene or α-carotene, preferably β-carotene.

According to the invention, the carotenoid without any provitamin A activity may be a mixture of carotenoids without any provitamin A activity. This mixture may be in any proportion. From among carotenoids without any provitamin A activity, mention may be made as an example of zeaxanthin, cryptoxanthin, lutein or lycopene.

More particularly, the carotenoid applied within the scope of the present invention is lycopene.

In other words, the carotenoid present in the combination of actives of the present invention comprises, or even is formed with lycopene.

A carotenoid according to the invention may also be astaxanthin.

The carotenoid used according to the invention may be of natural or synthetic origin. By natural origin is meant the carotenoid in the pure state or in a solution regardless of its concentration in said solution, obtained from a natural element such as a vegetable extract. For example, when the carotenoid is lycopene, it is possible to more particularly use a tomato extract.

Thus, according to a preferred embodiment of the invention, the carotenoid applied in a combination according to the invention is lycopene, preferably in a tomato extract, more preferentially a tomato extract rich in lycopene.

A tomato extract rich in lycopene for example comprises at least 5% of lycopene, more preferentially at least 7% of lycopene, still more preferentially at least 10% of lycopene by weight based on the total weight of the extract.

A tomato extract rich in lycopene advantageously comprises at least 10% of lycopene, by weight based on the total weight of the extract.

By «synthetic origin» is meant lycopene in the pure state or in a solution regardless of its concentration in said solution, obtained by chemical synthesis. The lycopene which may be used within the scope of the present invention may be in a cis or trans chemical form.

When the carotenoid is of natural origin, it may be obtained from vegetable substances from the entire plant cultivated in vivo or issued from an in vitro culture.

By «cultivated in vivo» is meant any culture of the conventional type i.e. in soil, in free air or in a greenhouse, or further off-ground.

By «culture in vitro», is meant the whole of the techniques known to one skilled in the art which artificially gives the possibility of obtaining a plant or a portion of a plant. The selection pressure imposed by the physico-chemical conditions during the growth of plant cells in vitro gives the possibility of obtaining a standardized plant material and available all along the year unlike plants cultivated in vivo.

Preferentially according to the invention, a plant from a culture in vivo is used. Any extraction method known to one skilled in the art may be used for preparing the carotenoid used according to the invention.

Very preferentially, in the case of lycopene, a tomato extract rich in lycopene is used.

Lycopene is also present in melon, guava and grapefruit.

Lycopene may be in an alcoholic solution, notably ethanolic solution. The carotenoid may also be in a lipid or lipo-alcoholic solution.

The lycopene may be in an aqueous suspension. For this, hydrodispersible forms may be used under cold or hot conditions.

Any other more complex ingredient based on lycopene may also be used for applying the invention.

Thus, by more complex ingredient is for example meant a primary composition comprising the lycopene and a whey protein. This primary composition is notably described in document WO 01/91588. This primary composition also bears the name of lactolycopene. It has the benefit of increasing bioavailability of lycopene and/or of being easily formulated in food supplements (sachet, gelatin capsule, tablet, dragee, soft capsule forms, . . . ).

Lactolycopene may notably be sold by Indena.

The amount of extract which may be used according to the invention depends of course on the sought effect and may therefore vary to a large extent.

The total content of carotenoid(s), preferably of lycopene, in a composition according to the invention may vary from 0.01% to 6% by weight, preferably from 0.02% to 4% by weight, more preferentially from 0.05% to 3% by weight, still more preferentially from 0.07% to 2% by weight, based on the total weight of the composition.

For example, a composition according to the invention may comprise a total content of carotenoid(s), preferably of lycopene, comprised between 0.09% and 0.1% by weight based on the total weight of the composition.

A composition according to the invention, as developed hereafter, may comprise at least one carotenoid, preferably lycopene, in an adjusted total concentration of carotenoid(s) for an administration at a content ranging from 0.1 mg/day to 10 mg/day, preferably from 0.5 mg/day to 8 mg/day, more preferentially from 0.8 mg/day to 6 mg/day.

For example, a composition according to the invention may comprise at least one carotenoid, preferably lycopene, in an adjusted concentration so that it is administered at a content ranging from 1 mg/day to 1.5 mg/day.

Thus, a combination of actives according to the invention advantageously comprises at least one oil comprising at least one polyunsaturated fatty acid, vitamin D and isolated lycopene and/or an extract rich in lycopene.

According to a preferred embodiment, a combination of actives according to the invention comprises fish oil and/or blackcurrant pip oil, vitamin D, and a tomato extract.

According to a further preferred embodiment, a combination of actives according to the invention comprises fish oil, blackcurrant pip oil, vitamin D and a tomato extract.

Preferably, a combination of actives according to the invention comprises, in addition to at least one polyunsaturated fatty acid, vitamin D and lycopene, vitamin C and/or vitamin E, preferentially vitamin C and vitamin E.

Zinc

A preferred combination of actives according to the invention also comprises zinc.

By «zinc», is meant zinc or one of its salts (zinc acetate, chloride, citrate, lactate, gluconate, lactate, oxide, carbonate or sulphate), in particular salts of Zn(II) and preferably complexed by one or several (poly)hydroxyacids such as gluconate.

According to a particular embodiment of the invention, the zinc is not a zinc oxide but a zinc salt.

Insofar that the product according to the invention is intended for oral application in an individual, the salts which may be applied should of course be selected for their complete innocuousness.

By Zn(II), is meant a zinc atom with a degree of oxidation of $Zn^{2+}$.

By (poly)hydroxyacid, is meant any carboxylic acid which comprises a saturated or unsaturated linear or branched hydrocarbon chain, preferably saturated and/or linear, comprising from 1 to 10 carbon atoms and from 1 to 9 hydroxy groups, and comprising from 1 to 4 carboxylic groups —C(O)—OH, for which at least one of said functions —C(O)—OH is in the form of a carbon/late —C(O)—O— complexed with the Zn atom, preferably Zn(II) atom.

More particularly, the zinc salt is complexed with two carbon/late groups such as the one of formula (I) R—C(O)—O—Zn—O—C(O)—R', as well as its solvates such as the hydrates and their enantiomers, R and R' being identical or different and representing a $(C_1$-$C_6)$(poly)hydroxyalkyl group.

Preferably, the compound of formula (I) is zinc gluconate.

The zinc content in a composition according to the invention may for example vary from 0.001% to 30% by weight, preferably from 0.05% to 20% by weight, and more preferentially from 0.1% to 10% by weight based on the total weight of the composition.

For example, a composition according to the invention may comprise a zinc content, comprised between 0.5% and 0.7% by weight based on the total weight of the composition.

A composition according to the invention, as developed hereafter, may comprise zinc in an adjusted concentration so that it is administered at a content ranging from 0.01 mg/day to 300 mg/day, preferably from 0.1 mg/day to 200 mg/day, more preferentially from 1 mg/day to 100 mg/day, still more preferentially from 3 mg/day to 10 mg/day.

For example, a composition according to the invention may comprise zinc in an adjusted concentration so that it is administered at a content ranging from 6 mg/day to 8 mg/day.

Antioxidant Agents

A combination of actives according to the invention may comprise, in addition to at least one polyunsaturated fatty acid and vitamin D, an antioxidant agent other than carotenoids.

Antioxidant agents are known to one skilled in the art.

The antioxidant agents may for example be selected from among curcuminoids; polyphenol compounds, flavonoids such as catechins; proanthocyanidins, anthocyanins, OPCS (procyanidolic oligomers); ubiquinones; coffee extracts containing polyphenols and/or diterpenes; chicory extracts; ginkgo biloba extracts; grape extracts rich in proanthocyanidins; pepper extracts; soya bean extract; cocoa; pomegranate; Emblica; CoenzymeQ10; selenium.

Anti-inflammatory Agent

A combination of actives according to the invention may comprise, in addition to at least one polyunsaturated fatty acid and vitamin D, an anti-inflammatory agent.

Anti-inflammatory agents are known to one skilled in the art.

An anti-inflammatory agent according to the invention may be selected from among flavonoids such as catechins, proanthocyanidins, anthocyanins, procyanidolic oligomers (OPC), flavanones, for example hesperidin.

In a particular embodiment, the combination of actives does not comprise any anti-inflammatory agent.

Probiotic and Prebiotic Microorganism

According to a particular embodiment, a composition according to the invention may further comprise at least one probiotic microorganism, at least one prebiotic or combinations thereof.

Specific examples of probiotic microorganisms suitable for the invention are microorganisms of the *Bifidobacterium* genus, such as *Bifidobacterium adolescentis, Bifidobacterium animalis, Bifidobacterium bifidum, Bifidobacterium breve, Bifidobacterium lactis, Bifidobacterium longum, Bifidobacterium infantis, Bifidobacterium pseudocatenulatum, Lactobacillus acidophilus* (LC1, NCFB 1748); microorganisms of the *Lactobacillus* genus, such as *Lactobacillus amylovorus, Lactobacillus casei* (Shirota), *Lactobacillus rhamnosus* (strain GG), *Lactobacillus brevis, Lactobacillus crispatus, Lactobacillus delbrueckii* (subsp. *bulgaricus, lactis*), *Lactobacillus fermentum, Lactobacillus helveticus, Lactobacillus gallinarum, Lactobacillus gasseri, Lactobacillus johnsonii, Lactobacillus paracasei, Lactobacillus plantarum, Lactobacillus rhamnosus, Lactobacillus salivarius, Lactobacillus alimentarius, Lactobacillus curvatus, Lactobacillus casei* subsp. *casei, Lactobacillus sake*, microorganisms of the *Lactococcus* genus such as *Lactococcus lactis, Lactococcus lactis* subspp. *lactis or cremoris*, microorganisms of the *Enterococcus* genus such as *Enterococcus faecalis* or *Enterococcus faecium*, microorganisms of the *Leuconostoc* genus, such as *Leuconostoc mesenteroides* subspp. dextranicum, microorganisms of the *Pediococcus* genus, such as *Pediococcus acidilactici*, microorganisms of the *Sporolactobacillus* genus, such as *Sporolactobacillus inulinus*, microorganisms of the *Streptococcus* genus, such as *Streptococcus salvarius* subsp. *thermophilus, Streptococcus thermophilus*, microorganisms of the *Staphylococcus* genus, such as *Staphylococcus carnosus, Staphylococcus xylosus*, microorganisms of the *Saccharomyces* genus, such as *Saccharomyces cerevisiae* or further *Saccharomyces boulardii*, microorganisms of the *Bacillus* genus, such as *Bacillus cereus* var. *toyo, Bacillus subtilis, Bacillus coagulans, Bacillus licheniformis*, microorganisms of the *Escherichia* genus, such as *Escherichia coli* strain nissle, microorganisms of the *Propionibacterium* genus, such as *Propionibacterium freudenreichii*, or combinations thereof.

The microorganisms may be formulated as powders, i.e. in a dry form, or as suspensions or solutions.

More particularly, this may be a probiotic microorganism selected from among microorganisms of the *Lactobacillus* sp. genus and/or *Bifidobacterium* sp., one of their fractions and/or one of their metabolites. As an illustration of these microorganisms, mention may more particularly be made of *Lactobacillus johnsonii, Lactobacillus rhamnosus, Lactobacillus paracasei, Lactobacillus casei, Bifidobacterium bifidum, Bifidobacterium breve, Bifidobacterium longum, Bifidobacterium animalis, Bifidobacterium lactis, Bifidobacterium infantis, Bifidobacterium adolescentis, Bifidobacterium pseudocatenulatum*, or combinations thereof.

The most particularly suitable species are *Lactobacillus johnsonii, Lactobacillus paracasei, Bifidobacterium adolescentis, Bifidobacterium longum* or *Bifidobacterum Lactis* NCC 2818 (further designated as Bb12 ATCC 27536) respectively deposited according to the Budapest treaty by the Institut Pasteur (28 rue du Docteur Roux, F-75024 Paris cedex 15) on 30.06.92, 12.01.99, 15.04.99, 15.0.99, 07.06.05 under the following designations CNCM I-1225, CNCM I-2116, CNCM I-2168, CNCM I-2170 and CNCM I-3446, and the species *Bifidobacterium longum* (BB536). The strain of *Bifidobacterium lactis* CNCM I-3446 may be obtained from Hansen (Chr. Hansen A/S, 10-12 Boege Alle, P.O. Box 407, DK-2970 Hoersholm, Denmark).

According to a particular embodiment of the invention, the composition comprises at least two different microorganisms notably probiotic, and/or metabolites and/or fractions thereof. These microorganisms may differ by their nature for example a bacterium and fungus, or else further by their family, their genus, their species, or only by their strain.

The prebiotics suitable for the invention may be selected from oligosaccharides produced from glucose, galactose, xylose, maltose, sucrose, lactose, starch, xylane, hemicellulose, inulin, gums, for example of the acacia type, or one of their mixtures. More particularly, the oligosaccharide comprises at least one fructo-oligosaccharide. More particularly, this prebiotic may comprise a mixture of fructo-oligosaccharide and of inulin.

In a particular embodiment, the combination of actives does not comprise any probiotic and/or prebiotic microorganism.

Cosmetic Composition Intended for Oral Administration and Kits

According to an aspect of the invention, a combination of actives according to the invention may be applied within a cosmetic composition adapted for oral administration.

The object of the present invention is particularly a cosmetic composition adapted for oral administration comprising a combination of actives as defined above.

By «cosmetic composition», is for example meant a nutritional composition, for example a food supplement, comprising at least one combination of actives according to the invention.

The expressions of «nutritional composition», «nutraceutical composition» or «cosmeceutical composition» are synonyms here.

By «food supplement», is meant to refer here to a foodstuff for which the purpose is to complete the normal food diet and which is a concentrated source of nutriments, i.e.

vitamins and/or minerals, and/or other substances having a nutritional or physiological effect, alone or combined, marketed as doses, i.e. the presentation forms such as gelatin capsules, lozenges, tablets, soft capsules, pills and other similar forms, as well as sachets of powder to be diluted, ampoules of liquid, flasks provided with a dropper and the other similar forms of liquid preparations or as beverages.

A preferred cosmetic composition according to the invention is a food supplement.

A preferred cosmetic composition according to the invention intended for oral administration comprises:

- at least one polyunsaturated fatty acid, the total content of polyunsaturated fatty acid being comprised between 1% and 80% by weight, preferably between 5% and 70% by weight, more preferentially between 10% and 60% by weight, still more preferentially between 20% and 50% by weight,
- vitamin D in a content comprised between 0.00001% and 0.15% by weight, preferably between 0.00005% and 0.1% by weight, more preferentially between 0.0001% and 0.1% by weight, still more preferentially between 0.0001% and 0.05% by weight,
- optionally zinc in a content comprised between 0.001% and 30% by weight, preferably between 0.05% and 20% by weight, more preferentially between 0.1% and 10% by weight, still more preferentially between 0.2% and 5% by weight, zinc preferably being in the form of zinc gluconate,
- optionally vitamin E in a content comprised between 0.001% and 10% by weight, preferably between 0.01% and 10% by weight, more preferentially between 0.1% and 5% by weight, still more preferentially between 0.2% and 2% by weight,
- optionally vitamin C in a content comprised between 0.001% and 30% by weight, preferably between 0.01% and 25% by weight, more preferentially between 0.1% and 20% by weight, still more preferentially between 1% and 15% by weight, and
- optionally at least one carotenoid, the total carotenoid content being comprised between 0.01% and 6% by weight, preferably between 0.02% and 4% by weight, more preferentially between 0.05% and 3% by weight, still more preferentially between 0.07% and 2% by weight, the percentages being given by weight based on the total weight of the cosmetic composition.

Another example of a preferred cosmetic composition according to the invention intended for oral administration consists in:

- at least one polyunsaturated fatty acid, the total content of polyunsaturated fatty acid being comprised between 1% and 80% by weight, preferably between 5% and 70% by weight, more preferentially between 10% and 60% by weight, still more preferentially between 20% and 50% by weight,
- vitamin D in a content comprised between 0.00001% and 0.15% by weight, preferably between 0.00005% and 0.1% by weight, more preferentially between 0.0001% and 0.1% by weight, still more preferentially between 0.0001% and 0.05% by weight,
- optionally zinc in a content comprised between 0.001% and 30% by weight, preferably between 0.05% and 20% by weight, more preferentially between 0.1% and 10% by weight, still more preferentially between 0.2% and 5% by weight, the zinc preferably being in the form of zinc gluconate,
- optionally vitamin E in a content comprised between 0.001% and 10% by weight, preferably between 0.01% and 10% by weight, more preferentially between 0.1% and 5% by weight, still more preferentially between 0.2% and 2% by weight,
- optionally vitamin C in a content comprised between 0.001% and 30% by weight, preferably between 0.01% and 25% by weight, more preferentially between 0.1% and 20% by weight, still more preferentially between 1% and 15% by weight, and
- optionally at least one carotenoid, the total carotenoid content being comprised between 0.01% and 6% by weight, preferably between 0.02% and 4% by weight, more preferentially between 0.05% and 3% by weight, still more preferentially between 0.07% and 2% by weight,
- optionally at least one excipient, preferably selected from glycerol monostearate, beeswax, soy lecithin or combinations thereof, the percentages being given by weight based on the total weight of the cosmetic composition.

Such a cosmetic composition adapted for oral administration, preferably a food supplement, may have the following contents:

| Active material | % by weight based on the total weight of the composition |
|---|---|
| Polyunsaturated fatty acid(s) | 35 to 37 (including omega 3 and omega 6) |
| Vitamin D3 | 0.0004 to 0.0006 |
| Vitamin C | 2.4 to 2.5 |
| Vitamin E | 0.4 to 0.5 |
| Carotenoid(s) (preferably lycopene) | 0.09 to 0.10 |
| Zinc (preferably as zinc gluconate) | 0.6 to 0.7 |

A composition according to the invention comprises a physiologically or cosmetically acceptable carrier.

A combination of actives and a composition according to the invention give the possibility, because of their oral administration, of improving the quality of the hair.

The invention does not relate to the therapeutic field.

The combination of actives according to the invention or the composition according to the invention is administered via an oral route.

The combinations of actives and compositions according to the invention, intended for oral administration, may notably comprise the whole or only a portion of the daily dose.

In the case of compositions suitable for oral administration, the use of an ingestible support is preferred. The ingestible support may be of a diverse nature according to the relevant type of composition.

For ingestion, many embodiments of oral compositions and notably of food supplements are possible.

The formulation of such compositions may be made by any usual method known to one skilled in the art.

Thus, a composition according to the invention may preferably assume the form of a dragee, a gelatin capsule, a suspension, a gel, an emulsion, a drinkable solution, a tablet to be swallowed or to be crunched, a capsule, notably a soft or hard capsule, a granule to be dissolved, a syrup, a tablet or a drinkable ampoule.

It may preferably appear as a soft or hard capsule, preferably as a soft capsule.

In particular, a combination of actives according to the invention may be applied in any forms of food supplements or either compacted powders or not. The powders may be diluted with water or in soda. According to a preferred embodiment, a composition according to the invention administered orally may be formulated as a dragee, a gelatin capsule, a gel, an emulsion, a tablet, a capsule, a hydrogel, an either compacted powder or not, a suspension or liquid solution.

The oral compositions may appear either in an anhydrous form, or in an aqueous form.

A combination of actives according to the invention may be formulated with the usual excipients for such oral compositions, such as food supplements, i.e. notably fatty and/or aqueous components, humectants, thickeners, preservatives, texturing agents, flavors and/or coating agents, antioxidants, preservatives and usual coloring agents in the field of food.

Of course, one skilled in the art will make sure upon selecting the optional excipients and formulation agents and/or their amount in such a way that the advantageous properties of the combination according to the invention or of the composition comprising the combination according to the invention are not or not substantially altered by the contemplated addition.

The formulation agents and excipients for an oral composition, and notably for food supplements are known in this field and are not here the object of a detailed description.

The invention also relates to a cosmetic kit or combination product for simultaneous, separate or spread out in time use, preferably a food supplement, comprising a first composition comprising a portion of the compounds forming the combination of actives according to the invention and a second composition comprising at least the other portion of the compounds forming said combination of actives.

This supplement may be formulated in such a way that both compositions are in the same forms or in different forms, for example selected from those mentioned above. Such a kit may notably be presented in a single and same package.

Cosmetic use of the Combination of Active Ingredients and of a Composition Comprising Them The object of the present invention is particularly the cosmetic use, via an oral route, of a combination of actives as defined above comprising at least one polyunsaturated fatty acid and vitamin D, in order to improve the quality of the hair.

In particular, the present invention relates to the use as defined above, wherein said at least one polyunsaturated fatty acid is applied as at least one oil selected from evening primrose oil, borage oil, blackcurrant pip oil, walnut oil, soya bean oil, fish oil, sunflower oil, wheat germ oil, hemp oil, fenugreek oil, echium oil, argan oil, rice bran oil, sesame oil, almond oil, hazelnut oil, chia seed oil, flax oil, olive oil, avocado oil, carthame oil, camelina oil, raspberry pip oil, cranberry seed oil, bilberry pip oil, *Rubus chamaemorus* Linne seed oil, sea buckthorn oil, cumin oil, kiwi pip oil, coriander oil, microalgae extract oil, zooplankton extract oil, crustacean and/or shellfish extract oil, or combinations thereof.

In an advantageous embodiment, the present invention relates to use as defined above, wherein said at least one polyunsaturated fatty acid is applied as blackcurrant pip oil and/or fish oil and/or said vitamin D is selected from vitamin D3 and vitamin D2, preferably vitamin D3.

In a particularly advantageous embodiment, the present invention relates to the use as defined above, characterized in that the combination of actives comprises, as an additional active, at least one compound selected from a vitamin other than vitamin D, a carotenoid, zinc or their combinations.

The object of the present invention is notably the use as defined above, wherein the combination of actives is applied within a cosmetic composition adapted for oral administration.

The contents are variable according to the form of the cosmetic composition in which is applied the combination of actives according to the invention.

The contents in the cosmetic composition, the form of the cosmetic composition and the daily administered doses are notably as defined above.

It is understood within the scope of the present invention that "the cosmetic use via an oral route" covers the use of compositions administered orally, these compositions for example being in the form of a food supplement. These compositions produce an effect, at the hair, aesthetically and as regards comfort, or further with a beauty purpose, for example with view to protecting it, to keeping it in good condition, and notably to embellish it, by improving the quality of the hair.

Method

The invention also relates to a cosmetic method for improving the quality of hair, comprising the oral administration to an individual of a combination of actives as defined above, of a cosmetic composition intended for oral administration as defined above or of a kit or combination product as defined above.

The methods according to the invention have the features of cosmetic methods notably in so far that they allow improvement in the aesthetics of the hair. Further, a combination of actives or a composition such as for example a food supplement according to the invention may be used daily for several months, without any medical prescription. The present invention is therefore clearly located outside the therapeutic field.

Advantageously, applying a method of the invention gives the advantages indicated earlier as being associated with the application of a combination of actives or of a composition according to the invention, and may notably improve the gloss of the hair and/or improve its hair styling capability and/or reducing hair loss and/or improving the growth of the capillary fiber and/or improving the volume of the hair and/or improving the quality of the capillary fiber.

A cosmetic method according to the invention may be applied, notably by administering a cosmetic composition as defined above.

A method of the invention may be daily applied for example, in an amount for example of one single administration per day or an administration twice a day, for example once in the morning and once in the evening, or three times a day, notably at each meal.

A cosmetic method according to the invention may for example be applied by daily administration of a composition for example formulated as a dragee, gelatin capsule, suspension, gel, emulsion, drinkable solution, tablet to be swallowed or crunched, capsule, notably a soft or hard capsule, granule to be dissolved, syrup, tablet or drinkable ampoule, in adequate amounts and number, according to their form.

An efficient amount of a combination of actives according to the invention may be administered in a single dose per day or in fractionated doses during the daytime, for example two to three times a day.

A method according to the invention may advantageously comprise a single administration. A cosmetic method may be applied over a period of time varying from one week to several weeks, or even several months, this period may moreover be repeated after periods of non-treatment, for several months or even several years.

As an example, the administration of a combination of actives according to the invention can be carried out in an amount of twice a day, generally over an extended period of at least four weeks, or even four to fifteen weeks, either comprising or not one or several periods of interruption or being repeated after an interruption period.

The ingredients are mixed, before their shaping, in the order and under conditions easily determined by one skilled in the art.

Thus, the cosmetic uses and/or methods according to the invention may improve the quality of the hair, in particular in men or women. The cosmetic uses and/or methods according to the invention particularly give the possibility of protecting aged hair, notably in men of more than 30 years of age or in women.

In the description and the examples which follow, the ranges of values labelled under the form of "between . . . and . . . " include the specified lower and upper limits.

Other features and advantages of the invention will become better apparent from the examples which follow, given as an illustration and not as a limitation.

EXAMPLES

Composition for an Oral Route in the Form of a Soft Capsule

The composition for an oral route has the formula given in the following table:

| Ingredients | Ingredient amount (in mg/capsule) | Percentage of the active material (by weight based on the total weight of the composition, capsule excluded) |
|---|---|---|
| Fish oil | 230.00 | 12.62 (polyunsaturated fatty acids) |
| Blackcurrent pip oil | 230.00 | 23.98 (polyunsaturated fatty acids) |
| Vitamin D3 | 0.12 | 0.00053 |
| Vitamin E | 4.10 | 0.43 |
| Vitamin C | 19.50 | 2.46 |
| Tomato extract | 5.50 | 0.097 (lycopene) |
| Zinc D-gluconate | 25.75 | 0.62 (zinc) |
| Excipients: | | |
| Glycerol mono-stearate | 30.03 | |
| Beeswax | 10.00 | |
| Soya lecithin | 10.00 | |

Calculation of the distribution of fatty acids of the oils used:
(1) Fish oil:
A soft capsule provides 71.3 mg of omega 3 including:
  34.5 mg of EPA (5,8,11,14,17-eicosapentaenoic acid) (omega 3),
  20.7 mg of DHA (4,7,10,13,16,19-docosahexaenoic acid) (omega 3).
(2) Blackcurrant pip oil:
A soft capsule provides 135.47 mg of polyunsaturated fatty acids including:
  80.73 mg of LA (linolenic acid) (omega 6),
  26.91 mg of GLA (γ-linolenic acid) (omega 6),
  22.77 mg of ALA (α-linolenic acid) (omega 3),
  5.06 mg of SDA (stearidonic acid) (omega 3).

The soft capsule for example has the following formula:

| Capsule | |
|---|---|
| Fish gelatin | 127.776 |
| Glycerol | 56.893 |
| Iron oxide | 2.051 |
| Titanium dioxide | 2.921 |
| Purified water | 21.082 |

A soft capsule according to the invention may be prepared in the following way.

The fish oil, the blackcurrant pip oil, the vitamin E, vitamin C, the tomato extract, the vitamin D3, the zinc gluconate and the excipients are mixed in the presence of nitrogen. The mixture is then homogenized, and then encapsulated in the soft capsule consisting of fish gelatin, glycerol, iron oxide, titanium dioxide and purified water.

The dosage is for example from 1 to 4 soft capsules per day, preferably 2 soft capsules/day.

This composition notably gives the possibility:
  of improving the gloss of the hair, in particular by promoting the growth of glossy hair,
  of improving the hair styling capability of the hair,
  of limiting hair loss, in particular by promoting anchoring of the hair,
  of improving the growth of the capillary fibre, in particular by participating in the normal growth of the hair and by promoting the thickness of the hair, notably by the growth of thick hairs,
  of improving the volume of the hair, in particular by promoting capillary abundance, by increasing the capillary mass and the density of the hairs, by increasing the diameter of the hairs, by preventing and/or limiting the formation of thin hairs,
  of improving the growth and the synthesis of a quality hair, in particular by preventing and/or limiting the formation of limp hairs and/or dull hairs, by improving the flexibility of the hairs, by improving the strength of the hair and by promoting the quality of the scalp (via the measurement of the microcirculation).

The invention claimed is:

1. A cosmetic method for improving the quality of the hair wherein the improving the quality of the hair comprises the improvement of the gloss of the hair and/or improvement of the hair styling capability of the hair and/or reduction of hair loss and/or improvement in the growth of the capillary fiber and/or improvement in the volume of the hair and/or improvement in the quality of the capillary fiber, consisting of administering via an oral route to an individual a cosmetic composition consisting of:
  polyunsaturated fatty acids, wherein said polyunsaturated fatty acids are in the form of blackcurrant pip oil and fish oil, the total content of polyunsaturated fatty acid being between 1% and 80%,
  vitamin D in a content comprised between 0.00001% and 0.15%,
  one carotenoid, said carotenoid being lycopene in the form of a tomato extract, the total carotenoid content being between 0.01% and 6%,
  zinc in a content between 0.001% and 30%,
  vitamin E in a content between 0.001% and 10%,
  vitamin C in a content between 0.001% and 30%, and
  excipients,
the percentages being given by weight based on the total weight of the cosmetic composition.

2. The method according to claim 1, wherein vitamin D is selected from the group consisting of vitamin D3 and vitamin D2.

3. The method according to claim 1, wherein said cosmetic composition is in the form of a dragee, a gelatin capsule, a suspension, a gel, an emulsion, a drinkable solution, a tablet to be swallowed or to be crunched, a capsule, a granule to be dissolved, a syrup, a tablet or a drinkable ampoule.

4. An oral cosmetic composition intended for oral administration for improving the quality of the hair consisting of:
   polyunsaturated fatty acids, wherein said polyunsaturated fatty acids are in the form of blackcurrant pip oil and fish oil, the total content of polyunsaturated fatty acid being between 1% and 80%,
   vitamin D in a content between 0.00001% and 0.15%,
   zinc in a content between 0.001% and 30%,
   vitamin E in a content between 0.001% and 10%,
   vitamin C in a content between 0.001% and 30%,
   one carotenoid, wherein said carotenoid is lycopene in the form of a tomato extract, the total carotenoid content being between 0.01% and 6%, and
   excipients,
   the percentages being given by weight based on the total weight of the cosmetic composition.

5. The cosmetic composition according to claim 4, wherein vitamin D is selected from the group consisting of vitamin D3 and vitamin D2.

6. The cosmetic composition according to claim 4, wherein the zinc is in the form of zinc gluconate.

7. The cosmetic composition according to claim 4, wherein said composition is in the form of a dragee, gelatin capsule, suspension, gel, emulsion, drinkable solution, tablet, capsule, granule, syrup or drinkable ampoule.

8. The cosmetic composition according to claim 6, wherein vitamin D is selected from the group consisting of vitamin D3 and vitamin D2.

9. The method according to claim 1, wherein the zinc is in the form of zinc gluconate.

* * * * *